(12) United States Patent
Tochio (10) Patent No.: US 9,314,966 B2
(45) Date of Patent: Apr. 19, 2016

(54) BANDSEAL FOR PEG-FILLED HARD CAPSULE

(75) Inventor: Shinji Tochio, Yamatokoriyama (JP)

(73) Assignee: QUALICAPS CO., LTD., Nara-ken (JP)

( * ) Notice: Subject to any disclaimer, the term of this patent is extended or adjusted under 35 U.S.C. 154(b) by 1298 days.

(21) Appl. No.: 12/071,088

(22) Filed: Feb. 15, 2008

(65) Prior Publication Data

US 2008/0254111 A1    Oct. 16, 2008

Related U.S. Application Data (60) Provisional application No. 60/901,328, filed on Feb. 15, 2007.

(51) Int. Cl.
    *A61K 9/48*    (2006.01)
    *B29C 65/00*   (2006.01)
    *A61J 3/07*    (2006.01)

(52) U.S. Cl.
    CPC .............. *B29C 66/01* (2013.01); *A61J 3/072* (2013.01); *A61K 9/4816* (2013.01); *A61K 9/4866* (2013.01); *A61K 9/4883* (2013.01); *Y10T 428/2998* (2015.01)

(58) Field of Classification Search
    None
    See application file for complete search history.

(56) References Cited

U.S. PATENT DOCUMENTS

| | | | |
|---|---|---|---|
| 3,984,494 A | | 10/1976 | Harréus et al. |
| 4,539,060 A | * | 9/1985 | Wittwer et al. ............ 156/275.1 |
| 5,776,987 A | * | 7/1998 | Rocco et al. .................. 514/778 |
| 2003/0108705 A1 | | 6/2003 | Duffield et al. |
| 2003/0166763 A1 | * | 9/2003 | Hoshi et al. .................... 524/459 |
| 2004/0151855 A1 | | 8/2004 | Duffield et al. |
| 2004/0242772 A1 | * | 12/2004 | Huth et al. ...................... 525/56 |
| 2005/0186268 A1 | * | 8/2005 | Hoshi et al. .................... 424/451 |
| 2008/0008750 A1 | | 1/2008 | Tochio et al. |
| 2008/0113019 A1 | | 5/2008 | Satokawa et al. |

FOREIGN PATENT DOCUMENTS

| | | |
|---|---|---|
| CA | 946281 A | 1/2008 |
| EP | 0110603 A2 * | 11/1983 |
| EP | 1 832 282 * | 12/2005 |
| FR | 1605150 A | 1/2008 |
| GB | 1298084 A | 1/2008 |
| JP | 06-157916 | 6/1994 |
| JP | 2000-202003 | 7/2000 |
| JP | 2001-170137 | 6/2001 |
| JP | 2003/327270 | 11/2003 |
| JP | 04-35569 | 2/2004 |
| JP | 2005-137935 | 6/2005 |
| JP | 07-15949 | 1/2007 |
| WO | WO2006/070578 | 7/2006 |
| WO | WO 2006070578 A1 * | 7/2006 |
| WO | WO2006/082842 | 8/2006 |
| WO | 2006/113568 A2 | 10/2006 |
| WO | 2006/132398 A1 | 12/2006 |

OTHER PUBLICATIONS

Supplementary European Search Report dated Mar. 4, 2011, issued against Application EP 08711167.0.
Communication pursuant to Article 94(3) EPC, issued Jun. 23, 2015 in corresponding European Application No. 08 711 167.0.
English translation of Japanese Application No. 2001-170137 dated Jun. 26, 2001.
Summons to attend oral proceedings issued Dec. 17, 2015 in corresponding European Application No. 08711167.0.
Summons to attend oral proceedings issued Dec. 17, 2015 in corresponding European Application No. 11007407.7.

* cited by examiner

*Primary Examiner* — David J Blanchard
*Assistant Examiner* — Daniel F Coughlin
(74) *Attorney, Agent, or Firm* — Wenderoth, Lind & Ponack, L.L.P.

(57) ABSTRACT

The present invention provides a band seal for hard capsules filled with PEG, particularly a low-molecular-weight PEG, PEG 200 to 600, the band seal being capable of effectively preventing content leakage through the gap between the body and cap of the capsule; and a liquid for preparing the band seal. The present invention further provides a hard capsule filled with PEG, particularly a low-molecular-weight PEG, PEG 200 to 600, the filled capsule being prevented content leakage through the gap between the body and cap of the capsule. The band seal can be prepared using a polyvinyl alcohol, a polyvinyl alcohol copolymer, or a mixture thereof as a main component.

14 Claims, 1 Drawing Sheet

BANDSEAL FOR PEG-FILLED HARD CAPSULE

FIELD OF THE INVENTION

The present invention relates to a band seal for a filled hard capsule, and particularly a band seal for a hard capsule filled with a polyethylene glycol (hereinafter sometimes also referred to as "PEG"); and a liquid for preparing the band seal. The present invention further relates to a hard capsule filled with PEG and sealed with a band seal, and a process for preparing the same.

BACKGROUND ART

Filled hard capsules in which the leakage or seepage of content is prevented have been desired as hard capsules filled with pharmaceuticals, health foods and other foods, cosmetics, agricultural chemicals, etc. Hard capsules filled with solids and thus free from liquid leakage problems may suffer deterioration of their oxygen- or water-susceptible contents if oxygen and water enter through the gap between the body and cap of the capsule. Therefore, a filled hard capsule in which the entry of oxygen and water through the gap is prevented has been desired.

Band seals have been used as a method to solve this problem. The band seal is a sealant (sealing agent) used to seal a fitting portion between the body and cap of a hard capsule after the contents are inserted in the capsule.

Polyethylene glycol (PEG), particularly a low-molecular-weight PEG with an average molecular weight of 200 to 600, has excellent solvent action and high absorptivity, and is therefore widely used as an excipient for drugs, quasi drugs, foods, etc. However, when PEG, which has a high moisture-absorptivity, is enclosed in a gelatin hard capsule that is weak under low-water-content conditions, the capsule film becomes fragile because of the reduced water content of the film. As a result, cracking is likely to occur over time.

Capsules formed of a water-soluble cellulose derivative, particularly hydroxypropyl methylcellulose (HPMC), as a film component have been proposed as non-gelatin hard capsules that can overcome the above-mentioned defects of gelatin hard capsules. However, it has been reported that when PEG is enclosed in an HPMC hard capsule that has high strength even under low-water-content conditions, PEG permeates and leaks out of the capsule film. Therefore, HPMC capsules are not suitable for use as hard capsules into which PEG or a composition comprising PEG is inserted.

To solve this problem, several hard capsules for use to contain PEG have been proposed. More specifically, hard capsules comprising at least one gelled polysaccharide selected from the group consisting of pullulan, hemicellulose, corn starch, carboxymethyl cellulose, and water-soluble salts thereof (Patent Document 1); hard capsules comprising pullulan gelled with a gelling agent (Patent Document 2); and hard capsules formed of a film comprising a polyvinyl alcohol as a base material (Patent Document 3) have been proposed as hard capsules suitable for use to contain PEG therein.

However, none of the above documents describe how to solve the problem of PEG leakage through the gap between the body and cap of the hard capsules.

Patent Document 1: Japanese Unexamined Patent Publication No. 2000-202003
Patent Document 2: Japanese Unexamined Patent Publication No. 2005-137935
Patent Document 3: Japanese Unexamined Patent Publication No. 2001-170137

DISCLOSURE OF THE INVENTION

An object of the present invention is to provide a band seal for a hard capsule filled with polyethylene glycol (PEG), particularly a low-molecular-weight PEG with an average molecular weight of 200 to 600, the band seal being capable of effectively preventing the contents of the capsule from leaking through the gap between the body and cap of the capsule; and a liquid for preparing the band seal. Another object of the present invention is to provide a hard capsule filled with PEG, particularly a low-molecular-weight PEG having an average molecular weight of 200 to 600, the filled capsule being prevented content leakage through the gap between the body and cap of the capsule; and a process for preparing such a filled hard capsule.

To achieve the above objects, the present inventors carried out extensive research, and found that when a band seal produced by using a polyvinyl alcohol (hereinafter sometimes also referred to as "PVA"), a polyvinyl alcohol copolymer (hereinafter sometimes also referred to as a "PVA copolymer"), or a mixture thereof is applied to a hard capsule filled with a polyethylene glycol (PEG) or a composition comprising PEG, the problematic leakage of PEG-containing content through the gap between the body and cap of the capsule can be overcome. The inventors further found that the use of this band seal can provide a filled hard capsule that can maintain high quality even when stored for a long period of time.

The present invention has been accomplished, based on the above findings. The present invention provides the following items.

(I) Band Seal and Liquid for Preparing the Band Seal (I-1) A band seal for a hard capsule filled with PEG or a composition comprising PEG, the band seal comprising a polyvinyl alcohol (PVA), a polyvinyl alcohol copolymer (PVA copolymer) or a mixture thereof in a proportion to effect band sealing.

(I-2) A band seal according to (I-1), wherein the PEG is a low-molecular-weight PEG with an average molecular weight of 200 to 600.

(I-3) A band seal according to (I-1) or (I-2) comprising sorbitol, in addition to the PVA, PVA copolymer or mixture thereof, in a proportion to effect band sealing.

(I-4) A band seal according to any one of (I-1) to (I-3), wherein the hard capsule is formed of a film comprising PVA, a PVA copolymer or a mixture thereof.

(I-5) A band seal according to (I-4), wherein the hard capsule is formed of a film comprising a gelling agent, or a gelling agent and a gelling aid, in addition to the polyvinyl alcohol, polyvinyl alcohol copolymer or mixture thereof.

(I-6) A liquid for preparing the band seal of (I-1) or (I-2), which is an aqueous solution containing the PVA, PVA alcohol copolymer or mixture thereof in a proportion to effect band sealing.

(I-7) A liquid for preparing the band seal of (I-3), which is an aqueous solution containing sorbitol, in addition to the PVA, PVA copolymer or mixture thereof, in a proportion to effect band sealing.

(I-8) A liquid for preparing the band seal according to claim (I-6) or (I-7), which has a viscosity of 100 to 5,000 mPa·s, as measured with a B-type rotational viscometer (using a No. 2 rotor for a viscosity of less than 500 mPa·s, a No. 3 rotor for a viscosity of at least 500 mPa·s and less than 2,000 mPa·s, and a No. 4 rotor for a viscosity of 2,000 mPa·s or more) at 23° C. at 60 rpm for 1 minute.

(II) Filled Hard Capsule Sealed with the Band Seal, and Preparation Process Therefor (II-1) A filled hard capsule formed by inserting PEG or a composition comprising PEG into a hard capsule and sealing a cap-to-body fitting portion of the capsule with the band seal of any one of (I-1) to (I-5).

(II-2) A filled hard capsule according to (II-1), wherein the PEG is a low-molecular-weight PEG with an average molecular weight of 200 to 600.

(II-3) A filled hard capsule according to (II-1) or (II-2), wherein the hard capsule is formed of a film comprising PVA, a PVA copolymer or a mixture thereof.

(II-4) A filled hard capsule according to (II-3), wherein the hard capsule is formed of a film comprising a gelling agent, or a gelling agent and a gelling aid, in addition to the PVA, PVA copolymer or mixture thereof.

(III) Process for Preparing a Filled Hard Capsule Sealed with the Band Seal (III-1) A process for preparing a filled hard capsule, comprising inserting PEG or a composition comprising PEG into a hard capsule, fitting a cap onto a body of the capsule, applying the band seal-preparation liquid of any one of (I-6) to (I-8) to the fitting portion, and drying to seal the capsule.

(III-2) A process according to (III-1), wherein the PEG is a low-molecular-weight PEG having an average molecular weight of 200 to 600.

(III-3) A process according to (III-1) or (III-2), wherein the hard capsule is formed of a film comprising PVA, a PVA copolymer, or a mixture thereof.

(III-4) A process according to (III-3), wherein the hard capsule is formed of a film comprising a gelling agent, or a gelling agent and a gelling aid, in addition to the PVA, PVA copolymer or mixture thereof.

(IV) Process for Sealing a Filled Hard Capsule (IV-1) A process for sealing a filled hard capsule, comprising applying the band seal-preparation liquid of any one of (I-6) to (I-8) to a cap-to-body fitting portion of the hard capsule filled with PEG or a composition comprising PEG, and drying to seal the capsule.

(IV-2) A process according to (IV-1), wherein the PEG is a low-molecular-weight PEG with an average molecular weight of 200 to 600.

(IV-3) A process according to (IV-1) or (IV-2), wherein the hard capsule is formed of a film comprising PVA, a PVA copolymer, or a mixture thereof.

(IV-4) A process according to (IV-5), wherein the hard capsule comprises a gelling agent, or a gelling agent and a gelling aid, in addition to the PVA, PVA copolymer or mixture thereof.

BEST MODE FOR CARRYING OUT THE INVENTION

One feature of the band seal of the present invention is that the band seal comprises a polyvinyl alcohol (PVA), a polyvinyl alcohol copolymer (PVA copolymer), or a mixture thereof in a proportion to effect band sealing.

Figure 1:
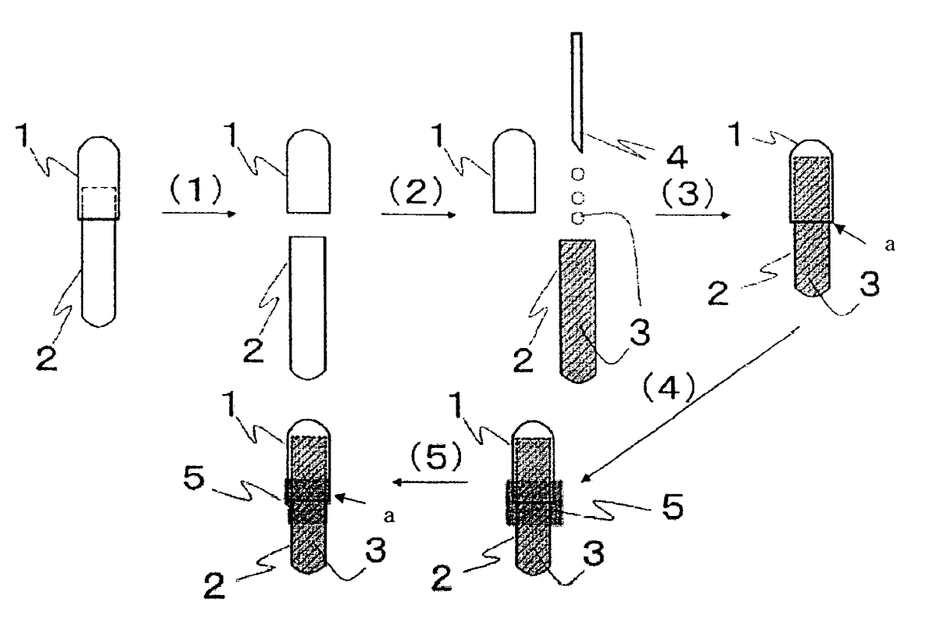
FIG. 1 is a schematic diagram showing the process of sealing a hard capsule with the band seal of the present invention. Reference numeral 1 denotes a cap of the hard capsule; reference numeral 2 denotes a body of the hard capsule; reference numeral 3 denotes the contents of the hard capsule; reference numeral 4 denotes a device for filling the contents into the hard capsule; reference numeral 5 denotes a band seal (sealing film); and reference letter "a" denotes the cut portion (edge) of the cap of the hard capsule.

In the present invention, the term "band seal" refers to a band-shaped film (reference numeral 5)(see FIG. 1) for sealing a filled hard capsule formed by joining a cap (reference numeral 1) to a body (reference numeral 2), the sealing film being formed by applying a band seal-preparation liquid to the outer peripheral surface portions of the body (reference numeral 2) and cap (reference numeral 1) in such a manner that the cut portion (edge) of the cap is approximately at the center of the application and the band seal-preparation liquid applied extends over both sides of the edge of the cap, followed by drying. In the present invention, the term "band seal-preparation liquid" refers to a liquid for preparing the band seal, more specifically, a solution of band seal-forming components in a solvent comprising water as a main component.

PVA refers to a polymer obtained by saponification of polyvinyl acetate. In general, there are two types of PVA: fully saponified PVA with a saponification degree of 97 mol % or more, represented by Formula (1) below; and partially saponified PVA with a saponification degree of 78 to 96 mol %, represented by Formula (2) below. In the present invention, both fully saponified PVA and partially saponified PVA are usable. Although the degree of saponification is not particularly limited, a partially saponified PVA with a saponification degree of 78 to 90 mol %, particularly about 87 to about 90 mol %, is preferably used.

[Formula (1)]

(1)

[Formula (2)]

(2)

In the formulas, n and m may be any integer.

The average degree of polymerization (n) of PVA is not particularly limited, as long as the film can be formed. In general, PVA preferably has an average degree of polymerization of about 400 to about 3,300, and particularly about 400 to about 2,000. The weight average molecular weight of PVA calculated from the above-mentioned average degree of polymerization and saponification degree is about 18,000 to about 175,000. However, the weight average molecular weight is not particularly limited thereto.

Examples of PVA copolymers include PVA copolymers obtained by copolymerizing the above-mentioned PVA or a derivative thereof with polymerizable vinyl monomer(s). Examples of PVA derivatives include amine-modified PVA, ethylene-modified PVA, PVA with a thiol group at the end (thiol-terminated modified PVA), and like known PVA derivatives. Thiol-terminated modified PVA is preferable.

Examples of polymerizable vinyl monomers include (1) acrylic acid, methacrylic acid, fumaric acid, maleic acid, and itaconic acid;

(2) sodium salts, potassium salts, ammonium salts, and alkylamine salts of the compounds described in (1);

(3) methyl methacrylate, methyl acrylate, ethyl methacrylate, ethyl acrylate, butyl methacrylate, butyl acrylate, isobutyl methacrylate, isobutyl acrylate, cyclohexyl methacrylate, cyclohexyl acrylate, 2-ethylhexyl methacrylate, 2-ethylhexyl acrylate, acrylonitrile, acrylamide, dimethylacrylamide, styrene, vinyl acetate, hydroxyethyl methacrylate, hydroxyethyl acrylate, esters of polyethylene glycol and methacrylic acid, esters of polyethylene glycol and acrylic acid, esters of polypropylene glycol and methacrylic acid, esters of polypropylene glycol and acrylic acid, N-vinylpyrrolidone, and acryloyl morpholine;

(4) compounds represented by the formula (wherein $R_1$ is a hydrogen atom or a methyl group, and $R_2$ is a hydrogen atom or an alkyl group having 1 to 4 carbon atoms).

At least one compound selected from the group consisting of the compounds described in (1) and (2) and at least one compound selected from the group consisting of the compounds described in (3) are preferably used in combination as polymerizable vinyl monomers. A combination of acrylic acid or methacrylic acid with methyl methacrylate is particularly preferable.

The PVA copolymer is preferably a high-molecular-weight copolymer comprising a partially saponified PVA as the skeleton and produced by copolymerizing the PVA with acrylic acid and methyl methacrylate. More preferably, the PVA copolymer is a PVA copolymer produced by copolymerizing a partially saponified PVA having an average degree of polymerization of about 300 to about 500 with polymerizable vinyl monomer(s) as mentioned above (particularly, acrylic acid and methyl methacrylate) in a weight ratio of about 6:4 to about 9:1. As polymerizable vinyl monomers, acrylic acid and methyl methacrylate are preferably used in a acrylic acid:methyl methacrylate ratio by weight of about 3:7 to about 0.5:9.5 to form a copolymer with a partially saponified PVA. A PVA copolymer produced by copolymerizing a partially saponified PVA having an average degree of polymerization of about 300 to about 500, methyl methacrylate, and acrylic acid in a weight ratio of 60 to 90:7 to 38:0.5 to 12 is particularly preferable. Specific examples of such PVA copolymers include POVACOAT (trade name, Type F, Type R and Type L; products of Daido Kasei Corp.), used in the Experimental Examples and Examples below. Such polyvinyl alcohol copolymers can be produced by the method described in WO02/17848.

The band seal of the invention may contain PVA or PVA copolymer(s) as mentioned above singly or as a mixture thereof. The mixing ratio of the PVA to the PVA copolymer is not particularly limited. The PVA:PVA copolymer mixing ratio (by weight) may be in the range of 100:0 to 0:100, preferably 99.9:0.1 to 0.1:99.9.

The band seal of the invention may contain sorbitol as a plasticizer, in addition to the PVA and/or PVA copolymer(s). The flexibility can be increased by incorporating the plasticizer. The proportion of sorbitol in the band seal is not particularly limited, as long as the band sealing properties of the PVA and/or PVA copolymers are not impaired. To achieve the above-mentioned effects, the proportion of sorbitol in the band seal (100 wt. %) may be 0.01 to 70 wt. %, preferably 0.01 to 35 wt. %, more preferably 0.01 to 30 wt. %, and particularly preferably 1 to 30 wt. % as the concentration.

In the present invention, the term "band sealing properties" refers to a property of the band seal capable of forming a film to seal the body and cap of a hard capsule (film-forming capability) and a property thereof capable of preventing content leakage through the fitting portion between the body and cap of the capsule by sealing with the film (leakage-preventing capability).

The "band sealing properties" can be evaluated by applying a band seal-preparation liquid sample to seal (band-seal) the fitting portion between the cap and body of a capsule filled with polyethylene glycol (PEG400) having an average molecular weight of 400; leaving the capsule on white paper at 25° C. in a relative humidity of 40% for 12 hours; and checking whether the contents have leaked through the band seal portion. The content leakage can be evaluated according to the following criteria, as described in Experimental Example 4:

(a) After the sealed filled hard capsule is left for 12 hours, whether any adhesion of the content (PEG400) is observed on the area of the white paper in contact with the capsule.

(b) When the sealed filled hard capsule is rolled on the white paper after being left on the paper for 12 hours, whether any adhesion of the contents (PEG400) is observed on the white paper.

If no adhesion of the content to the white paper, i.e., no content leakage, is observed in (a) and (b), the liquid is evaluated as "having band sealing properties". If any content leakage is observed in (a) or (b), the liquid is evaluated as "having no band sealing properties".

Examples of capsules that can be used in such a band sealing-property evaluation test include hard capsules comprising a PVA copolymer as a base material, as described below in Example 1, and hard capsules comprising PVA as a base material, as described below in Example 3. When using a hard capsule of Size No. 0 according to Japanese pharmacopoeia, the amount of PEG 400 filled in the capsule may be, for example, 600 µL. The amount of PEG 400 filled in a hard capsule of Size No. 1 may be, for example, 470 µL.

As long as the effects of the invention, i.e., band sealing properties, are not impaired, the band seal may optionally contain, in addition to the above components, additives usually used in the preparation of hard capsules, such as coloring agents (e.g., titanium oxide, red iron oxide, coal-tar based coloring agents), opacifying agents, and fragrances. Considering the band sealing properties, the proportion of such additives in the band seal can be appropriately selected from the range of 0.1 to 7 wt. %.

A band seal-preparation liquid is usually used to form the band seal on a hard capsule. The band seal-preparation liquid can be prepared by dissolving the band seal component(s) in water, a hydrophilic solvent, or a mixture of water and a hydrophilic solvent at room temperature or while heating (at about 30° C. to about 60° C.). A mixture of water and a hydrophilic solvent is preferably used. Examples of hydrophilic solvents include organic solvents that are compatible with water. Specific examples thereof include lower alcohols having 1 to 6 carbon atoms, and preferably 1 to 4 carbon atoms, such as ethanol, and isopropanol. Ethanol is preferable. When a mixture of water and a hydrophilic solvent is used to prepare a band seal-preparation liquid, the proportion of the hydrophilic solvent in the mixture may be, for example, 5 to 80 wt. %, preferably 8 to 65 wt. %, and more preferably 10 to 50 wt. %, based on the total weight of the mixture as 100 wt. %.

The band seal-preparation liquid is usually adjusted to a final viscosity of 100 to 5,000 mPa·s. In the present invention, the viscosity refers to a viscosity as measured with a B-type rotational viscometer (using a No. 2 rotor for a viscosity of less than 500 mPa·s, a No. 3 rotor for a viscosity of at least 500 mPa·s and less than 2,000 mPa·s, and a No. 4 rotor for a viscosity of at 2,000 mPa·s or more) at 23° C. at 60 rpm for 1 minute.

By using the band seal-preparation liquid having a viscosity within the above-mentioned range, a band seal having a high sealing force can be formed on the fitting portion between the body and cap of the filled hard capsule. Furthermore, when producing the band seal, inconvenient thread formation does not occur and the liquid is easy to handle. When the viscosity of the band seal-preparation liquid is remarkably lower than the above-mentioned range (100 to 5,000 mPa·s), it is difficult to apply the band seal-preparation liquid to the fitting portion of the filled hard capsule without dripping. As a result, a band seal with an excellent sealing force capable of achieving the effect of the present invention may not be formed. When the viscosity of a band seal-preparation liquid is remarkably higher than the above-mentioned range (100 to 5,000 mPa·s), the viscosity is too high to form a band seal using a machine. The band seal-preparation liquid preferably has a viscosity of 125 to 4,700 mPa·s, and more preferably 150 to 4,500 mPa·s.

The viscosity of the band seal-preparation liquid can be easily adjusted by adjusting the concentration of PVA and/or PVA copolymer in the band seal-preparation liquid, as described below in Experimental Example 3.

The viscosity may vary according to the kind and degree of polymerization of PVA and/or PVA copolymer used. However, when PVA is used alone, the concentration of PVA in the band seal-preparation liquid may usually be, for example, 4 to 31 wt. %, preferably 5 to 30 wt. %, and more preferably 6 to 29 wt. %. When a PVA copolymer is used alone, the concentration of the PVA copolymer in the band seal-preparation liquid may usually be, for example, 5 to 27 wt. %, preferably 6 to 26 wt. %, and more preferably 7 to 25 wt. %. When the PVA and PVA copolymer are used in combination, the viscosity can be adjusted based on the above-mentioned proportions of these components, considering the above-mentioned viscosity (100 to 5,000 mPa·s).

When the band seal contains sorbitol, the concentration of sorbitol in the band seal-preparation liquid can be appropriately selected according to the above-mentioned proportion of sorbitol in the band seal. More specifically, the band seal-preparation liquid is preferably prepared in such a manner that the resulting band seal (100 wt. %) contains sorbitol in a concentration of 0.01 to 70 wt. %, preferably 0.01 to 35 wt. %, more preferably 0.01 to 30 wt. %, and particularly preferably 1 to 30 wt. %, considering that the band seal-preparation liquid preferably has a viscosity of 100 to 5,000 mPa·s.

The band seal of the invention is suitable as a band seal for a hard capsule filled with polyethylene glycol (PEG) or a composition comprising a polyethylene glycol.

PEG is not particularly limited, and examples thereof include PEG having an approximate average molecular weight of 20,000 or less. More specifically, PEG having an average molecular weight of 200, 400, 600, 800, 1,000, 1,500, 2,000, 3,000, 4,000, 6,000, 8,000, or 20,000 can be mentioned as examples. PEG having such an average molecular weight is sold by various manufacturers under the common denotation "polyethylene glycol OOO" (in which OOO denotes the approximate average molecular weight of the PEG). Such PEG can be used singly or in a combination of two or more. In particular, a low-molecular-weight PEG having an average molecular weight of 200 to 600 ("PEG 200 to 600") is preferably used as a component enclosed in the hard capsule. That is, when using the band seal of the invention, problematic leakage does not occur even when the capsule contains PEG 200 to 600. The effects of the present invention can thus be more effectively provided.

The average molecular weight of PEG can be measured according to the following test method shown in "Japanese Pharmaceutical Excipients" and "Japanese pharmacopoeia", provided by the Japan Ministry of Health, Labour and Welfare.

Test on the Average Molecular Weight 300 mL of newly distilled pyridine is accurately weighed and placed into a 1 L light-resistant bottle with a ground-in stopper, and 42 g of phthalic anhydride is added. After vigorously shaking the bottle to dissolve the phthalic anhydride, the solution is allowed to stand for at least 16 hours. 25 mL of this solution is accurately weighed and placed into an about 200-mL pressure bottle with a ground-in stopper. After about 0.8 to about 15 g of a PEG sample is accurately weighed and added, the bottle is sealed, wrapped with a strong cloth, and immersed in a water bath heated to 98±2° C. in such a manner that the liquid in the bottle is under the water level of the bath. After the water bath is maintained at 98±2° C. for 30 minutes, the bottle is removed from the water bath and allowed to cool in the air to room temperature. Subsequently, 50 mL of a 0.5 mol/L sodium hydroxide solution is precisely added, 5 drops of a pyridine solution (1→100) of phenolphthalein are added, and the resulting liquid is titrated with a 0.5 mol/L sodium hydroxide solution. Titration is terminated when the liquid can maintain a pale red color for 15 seconds. A blank test is carried out in the same manner as above.

$$\text{Average Molecular Weight} = (\text{Amount}(g) \text{ of the Test PEG Sample} \times 4000)/(a-b)$$

a: Consumption (mL) of the 0.5 mol/L sodium hydroxide solution in the blank test b: Consumption (mL) of the 0.5 mol/L sodium hydroxide solution in the PEG sample test The contents of the hard capsule may be PEG or any composition that comprises at least PEG, as described above. Examples of such compositions include, but are not limited to, drugs for human beings or animals, quasi drugs, cosmetics, and foods. Although the proportion of PEG in the composition is not particularly limited, it is usually 0.01 to 99.99 wt. %, and preferably 0.05 to 99.95 wt. %.

The shape of the contents filled in the capsule is not particularly limited, either. Examples of shapes include liquids, gels, powders, granules, tablets, pellets, and mixtures thereof.

When the hard capsule is filled with a pharmaceutical, the pharmaceutical may be, for example, one or two or more kinds of pharmaceutical ingredients selected from nourishment tonics, antipyretics/analgesics/anti-inflammatory drugs, psychotropic drugs, anti-anxiety drugs, antidepressant drugs, hypnotic/sedative drugs, antispasmodic drugs, drugs acting on the central nervous system, cerebral metabolism improvers, cerebral circulation improvers, antiepileptic drugs, sympathetic nerve stimulants, digestives, antacids, antiulcer drugs, antitussive/expectorant drugs, antiemetic drugs, respiration promoters, bronchodilators, antiallergic drugs, drugs for dentistry and oral cavity, antihistamic drugs, cardiotonic drugs, antiarrhythmic drugs, diuretic drugs, antihypertensive drugs, vasoconstrictors, coronary vasodilators, peripheral vasodilators, antihyperlipidemic drugs, cholagogues, antibiotics, chemotherapeutic drugs, antidiabetic drugs; antiosteoporotic drugs, antirheumatic drugs, skeletal muscle relaxants, spasmolytic drugs, hormone preparations, alkaloid narcotics, sulfa drugs, anti-gout drugs, anticoagulant drugs, antineoplastic drugs, and the like. Such pharmaceutical ingredients are not particularly limited, and a wide variety of known ones can be used. Examples thereof include ingredients described in paragraphs [0055] to [0060] of WO 2006/070578.

When the hard capsule is filled with a food, examples of such foods include, but are not limited to, functional ingredients such as docosahexaenoic acid, eicosapentaenoic acid, α-lipoic acid, royal jelly, isoflavone, *agaricus*, acerola, aloe, aloe vera, turmeric, L-carnitine, oligosaccharide, cacao, catechin, capsaicin, chamomile, agar, tocopherol, linolenic acid, xylitol, chitosan, GABA, citric acid, *chlorella*, glucosamine, ginseng, coenzyme Q10, brown sugar, collagen, chondroitin, bracket fungus, squalene, stevia, ceramide, taurine, saponin, lecithin, dextrin, *Houttuynia cordata*, niacin, *Bacillus natto*, bittern, lactic acid bacteria, saw palmetto, honey, *Coix lacrymajobi* var. *ma-yuen*, ume extract, pantothenic acid, hyaluronic acid, vitamin A, vitamin K, vitamin C, vitamin D, vitamin B1, vitamin B2, vitamin B6, vitamin B12, quercetin, protein, propolis, mulukhiya, folic acid, lycopene, linoleic acid, rutin, and *Ganoderma lucidum*.

The filling of the contents in the hard capsule can be performed by using a per se known capsule-filling machine, such as a fully automatic capsule-filling machine (model name: "LIQFIL super 80/150", product of Shionogi Qualicaps Co., Ltd.), and a capsule-filing and sealing machine (model name: LIQFIL super FS, product of Shionogi Qualicaps Co., Ltd.), etc.

The filled hard capsule to which the band seal of the invention is applied is a capsule filled with PEG or a composition comprising PEG, and formed of a film which is physicochemically stable against PEG and is free of problems such as weakening due to reduced water content as in gelatin, or leakage of PEG through the film as in water-soluble cellulose derivatives.

Examples of such hard capsules include those formed of a film comprising PVA, a PVA copolymer, or a mixture thereof. Also usable are hard capsules formed using a gel comprising at least one polysaccharide selected from the group consisting of pullulan, hemicellulose, corn starch, carboxymethyl cellulose, and water-soluble salts thereof, as described in Japanese Unexamined Patent Publications Nos. 2000-202003 and 2005-137935.

Pullulan, hemicellulose, corn starch, and carboxymethyl cellulose are widely used as additives for foods, drugs, cosmetics, etc., and are commercially available. Hemicellulose is preferably a soybean-derived hemicellulose. "Hemilose", a product of Fuji Oil Co., Ltd., is particularly preferable. Water-soluble salts thereof may be any salt that dissolves in water. Examples thereof include alkali metal salts such as sodium salts and potassium salts.

In general, the hard capsule can be produced by an injection molding method or a dipping method. The dipping method is a capsule manufacturing method that makes: use of the gelation of the hard capsule film-forming base material (hard capsule-preparation liquid) by a temperature difference. If the base material has no gelling capability, a gelling agent is added.

The gelling agent is appropriately selected according to the compatibility with the hard capsule base material used, such as PVA, a PVA copolymer, pullulan, hemicellulose, corn starch, carboxymethyl cellulose or a water-soluble salt thereof as mentioned above. Specific examples of gelling agents include carrageenan, tamarind seed polysaccharide, pectin, xanthane gum, locust bean gum, curdlan, gelatin, furcellaran, agar, gellan gum, and the like. Such gelling agents can be used singly or in a combination of two or more.

Among the above gelling agents, carrageenan has a particularly high gel strength and can produce an excellent gelatinizing effect in the presence of specific ions, even when used in a small amount. Therefore, carrageenan is the most preferable gelling agent. In general, three types of carrageenan, i.e., kappa-carrageenan, iota-carrageenan, and lambda-carrageenan, are known. In the present invention, kappa-carrageenan and iota-carrageenan with gelatinizing abilities can be preferably used. Pectin can be classified into LM pectin and HM pectin according to the esterification degree difference; and gellan gum can also be classified into acylated gellan gum (native gellan gum) and deacylated gellan gum according to the acylation. In the present invention, any of the above can be used, regardless of type.

To produce the hard capsule, a gelling aid can also be selectively used according to the kind of gelling agent used. When kappa-carrageenan is used as the gelling agent, the gelling aid that can be used in combination therewith is, for example, a compound capable of forming in water one or two or more kinds of ions selected from potassium ion, ammonium ion and calcium ion, such as potassium chloride, potassium phosphate, ammonium chloride, ammonium acetate, or calcium chloride. When iota carrageenan is used as the gelling agent, the gelling aid that can be used in combination therewith is, for example, a compound capable of forming calcium ions in water, such as calcium chloride. When gellan gum is used as the gelling agent, the gelling aid that can be used in combination therewith is, for example, a compound capable of giving one or two or more kinds of ions selected from sodium ion, potassium ion, calcium ion, magnesium ion in water, such as sodium chloride, potassium chloride, calcium chloride, magnesium sulfate. Further, citric acid or sodium citrate can be used as an organic acid or a water-soluble salt thereof.

When PVA, a PVA copolymer, or a mixture thereof is used as the hard capsule component, the gelling agent preferably used with such a component is carrageenan, tamarind seed polysaccharide, xanthane gum, locust bean gum, or gellan gum. Carrageenan is particularly preferable. The gelling aid preferably used with such a gelling agent is, for example, potassium chloride.

When the hard capsule (capsule film) used in the invention comprises a gelling agent as mentioned above, the gelling agent content of the capsule may be, for example, 0.05 to 10 wt. %, preferably 0.1 to 5 wt. %, more preferably 0.2 to 2.5 wt. %, and further preferably 0.3 to 2 wt. %, based on the dry weight of the capsule film as 100 wt. %. When the hard capsule further comprises a gelling aid such as potassium chloride, the gelling aid content may be, for example, 2.2 wt. % or less, preferably 0.1 to 1.5 wt. %, more preferably 0.2 to 1 wt. %, and further preferably 0.3 to 0.8 wt. %.

The hard capsule may optionally comprise a plasticizer, sequestering agent, opacifying agent, coloring agent, and fragrance, in addition to the above-mentioned components (PVA, a PVA copolymer or mixture thereof, optionally together with a gelling agent and a gelling aid).

Any plasticizer that can be used for drugs and foods can be used as the plasticizer. Examples of such plasticizers include dioctyl adipate, adipic acid polyester, epoxidated soybean oil, diester of epoxyhexahydrophthalic acid, kaolin, triethyl citrate, glycerol, glycerol fatty acid ester, sesame oil, a mixture of dimethylpolysiloxane and silicon dioxide, D-sorbitol, medium-chain triglyceride, corn starch-derived liquid sugar alcohol, triacetin, concentrated glycerin, castor oil, phytosterol, diethyl phthalate, dioctyl phthalate, dibutyl phthalate, butyl phthalyl butyl glycolate, propylene glycol, polyoxyethylene (105) polyoxypropylene (5) glycol, Polysorbate 80, polyethylene glycols having an average molecular weight of 1,500, 400, 4,000, 600, and 6,000 (PEG1500, PEG400, PEG4000, PEG600, PEG6000), isopropyl myristate, a mixture of cottonseed oil and soybean oil, glyceryl monostearate, isopropyl linoleate, and the like. When using a plasticizer, the plasticizer content of the hard capsule (capsule film) of the invention is usually 15 wt. % or less, preferably 13 wt. % or less, more preferably 11 wt. % or less, and further preferably 8 wt. % or less, based on the dry weight of the capsule film as 100 wt. %.

Examples of sequestering agents include ethylenediaminetetraacetic acid, acetic acid, boric acid, citric acid, gluconic acid, lactic acid, phosphoric acid, tartaric acid, or salts thereof, metaphosphate, dihydroxyethylglycine, lecithin, β-cyclodextrin, and combinations thereof.

Any opacifying agent and fragrance that can be used for drugs or foods can be used as the opacifying agent and fragrance.

The hard capsule used in the invention can be produced according to a usual immersion method. More specifically, a capsule-forming pin is immersed into an aqueous solution containing the above-mentioned components (hereinafter referred to as a "capsule-preparation solution") as an immersion fluid; and the pin is then withdrawn therefrom. A film formed on the outer surface of the capsule-forming pin using the capsule-preparation solution is cooled to form a gel, followed by drying to produce a hard capsule. The aqueous solution is not limited to a solution using water as the solvent, and may be an aqueous solution containing ethanol in a proportion of 0.5 to 40 volume %.

The concentration of the components in the capsule-preparation solution can be suitably adjusted according to the above-mentioned proportions of the components of the hard capsule film. More specifically, the proportion of the essential component selected from PVA, PVA copolymers, pullulan, hemicellulose, corn starch, carboxymethyl cellulose, and water-soluble salts (hereinafter sometimes simply referred to as "essential component.") is 1 to 60 wt. %, preferably 5 to 50 wt. %, and more preferably 10 to 30 wt. %. When PVA, a PVA copolymer, or a mixture thereof is used as a component to form the hard capsule film, the concentration of the component in the capsule-preparation solution may be 5 to 30 wt. %, 10 to 28 wt. %, or 16 to 24 wt. %, based on the total weight of the PVA and PVA copolymer used.

When a gelling agent is used, the concentration of the gelling agent in the capsule-preparation solution may be, for example, 0.01 to 2 wt. %, preferably 0.02 to 1 wt. %, and more preferably 0.03 to 0.5 wt. %. When a gelling aid is used, the concentration of the gelling aid in the capsule-preparation solution may be, for example, 0.01 to 0.5 wt. %, preferably 0.02 to 0.3 wt. %, and more preferably 0.03 to 0.2 wt. %.

The amount of solvent (water or water-containing ethanol) in the capsule-preparation solution is not limited. The solvent may be used, for example, in such a proportion that the obtained capsule-preparation solution has a viscosity of 100 to 20,000 mPa·s, and preferably 300 to 10,000 mPa·s, as measured at the temperature of the immersion fluid (30° C. to 80° C., preferably 40° C. to 60° C.) used for the immersion of the capsule-forming pin. The solvent is preferably used in such a proportion that the viscosity of the obtained capsule-preparation solution as measured at 52° C. is 300 to 3,600 mPa·s, more preferably 500 to 3,100 mPa·s, further preferably 500 to 2,600 mPa·s, even more preferably 500 to 2,000 mPa·s, and particularly preferably 500 to 1,500 mPa·s. The viscosity specified in the present invention refers to the viscosity as measured with a B-type rotational viscometer (using a No. 2 rotor for a viscosity of less than 500 mPa·s, a No. 3 rotor for a viscosity of at least 500 mPa·s and less than 2,000 mPa·s, and a No. 4 rotor for a viscosity of 2,000 mPa·s or more) at 23° C. at 60 rpm for 1 minute (the same applied hereinafter). The solvent content is usually 60 to 90 wt. %, and preferably 70 to 85 wt. %.

When preparing the capsule-preparation solution, the order of dissolving the components is not limited. The essential component may be dissolved first, or the gelling agent and gelling aid may be dissolved first. The melting temperature is not particularly limited, but a temperature of 60° C. or more is usually preferable in view of the solubility of the components.

Preferably, tiny bubbles are removed from this capsule-preparation solution by degassing under reduced pressure, ultrasonic degassing, or allowing the solution to stand, and the solution is formed into a capsule at 50° C. to 60° C. according to the immersion methods.

After the capsule-forming pin is withdrawn from the capsule-preparation solution, gelation can be performed by heating or cooling according to the properties of the gelling agent used. For example, when carrageenan is used as a gelling agent, a gel can be formed more quickly by being allowed to cool. The gelled capsule-preparation solution is dried by air-drying, etc., and completely solidified. The solid is released from the pin mold and cut to a predetermined length to give a hard capsule (body and cap). In the above process, the drying may also be performed by heating at about 50° C. to about 80° C. By applying edible oil or the like as a release agent, the mold-releasability of the obtained capsule (body and cap) is increased. As a result, the obtained hard capsule can be more easily released.

In general, the size of hard capsules includes Size No. 00, No. 0, No. 1, No. 2, No. 3, No. 4, No. 5, etc. Hard capsules of any size can be used in the present invention.

After the contents (PEG or composition comprising PEG) are filled into the body of the hard capsule, the cap is fitted onto the body to connect the body and cap of the capsule. Subsequently, the band seal-preparation liquid is applied at an even width onto the surfaces of the body and cap in the circumferential direction in such a manner that the edge of the cap is at the center of the application and the solution applied extends over both sides of the edge of the cap, one to several times, and preferably once or twice to seal the fitting portion, thus forming a band seal at the fitting portion between the body and cap of the hard capsule (see FIG. 1).

In fitting the body and cap of the hard capsule, in general, the width of the fitting portion where the outer periphery of the body overlaps with the inner periphery of the cap is preferably in the range of about 4.5 to 6.5 mm for Size No. 3 capsules and about 4 to about 6 mm for Size No. 4 capsules, in the axial direction of the capsule. In general, the sealing width is preferably about 1.5 to about 3 mm for Size No. 3 capsules, and about 1.5 to about 2.8 mm for Size No. 4 capsules.

The band seal-preparation liquid can usually be used at room temperature or with heating. To prevent liquid leakage from the hard capsule, a seal-preparation solution maintained at a temperature in the range of about 23° C. to about 45° C., more preferably about 23° C. to about 35° C., and most preferably about 25° C. to about 35° C. is preferably used. The temperature of the seal-preparation solution can be controlled by a per se known method using a panel heater, warm-water heater, etc. It is preferable to control the temperature using a circulating-type hot-water heater or a circulating-type hot-water heater as modified from a seal-pan unit of the above-mentioned integral capsule sealing machine, because such a heater can permit fine adjustment of the temperature range. Because an alcohol in the seal-preparation solution, such as ethanol, vaporizes under some temperature conditions, it is desirable to appropriately replenish such alcohol to maintain the composition of the seal-preparation solution.

Sealing of the hard capsules can be conducted by use of a per se known capsule filling machine, such as the above-mentioned capsule filling and sealing machine (model name: HICAPSEAL 40/100, product of Shionogi Qualicaps Co., Ltd.).

When the thus obtained hard capsule of the invention is filled with PEG, particularly a low-molecular-weight PEG such as PEG 200 to 600, leakage of PEG does not occur, and the capsule has excellent working efficiency. Furthermore, even when the capsule is filled with a glycerol fatty acid ester or medium chain fatty acid triglyceride of such a low molecular PEG, the capsule film does not weaken. Therefore, the capsule of the invention is also suitable for use to contain a pharmaceutical composition comprising such a low-molecular-weight PEG, a glycerol fatty acid ester or medium chain fatty acid triglyceride thereof as an excipient. Furthermore, even when the water content of the capsule film is reduced, the capsule can maintain good strength, and problems such as cracking do not occur. Therefore, the capsule is also suitable for use to contain a drug of high water absorptivity, and/or a drug preferably stored under low-water-content conditions. Furthermore, because substantially no steam or oxygen passes through the capsule film, the capsule is also suitable for use to contain a water-reactive substance or an oxidizable substance.

EXAMPLES

Experimental Examples and Examples are given below to illustrate the invention. However, the present invention is not limited thereto or thereby. In the following Examples, "%" means "% by weight", unless otherwise specified.

Experimental Example 1

Selection of Raw Materials for the Band Seal (Part 1)

Using a polyethylene glycol with an average molecular weight of 400 (PEG400) as polyethylene glycol (PEG), high-molecular compounds and plasticizers capable of forming a PEG-insoluble film, were researched according to the method below.

As shown in Table 1, the high-molecular compounds used were polyvinylpyrrolidone, copolyvidone, methylcellulose, gum arabic, gelatin, hydroxypropyl methylcellulose, hydroxypropylcellulose, pullulan, agar, a PVA copolymer (POVACOAT Type F, product of Daido Kasei Corp., viscosity: 5.5 mPa·s, as measured at 25° C. using a 5% aqueous solution of the copolymer), and PVA (JP-05, product of Japan Vam & Poval Co., Ltd., average degree of polymerization: 500, partially saponified PVA: saponification degree 87 to 89 mol %); and the plasticizers used were glycerol, triethyl citrate, propylene glycol, triacetin, Polysorbate 80, sorbitol, medium-chain triglyceride; and sesame oil.

0.5 g each of the high-molecular compounds and plasticizers were placed into separate test tubes. 5 mL of PEG400 was added to each test tube. After stirring with a mixer, the resulting mixtures were inspected with the naked eye and the high-molecular compounds and plasticizers were evaluated for their solubility in PEG400. If no solids or no liquid separation was observed with the naked eye, the high-molecular compound or plasticizer was evaluated as "dissolved". If some solids or liquid separation was observed, the high-molecular compound or plasticizer was evaluated as "not dissolved (insoluble)". The results are shown in Table 1.

TABLE 1

Test Results of Solubility in PEG400

| | Test substances | Evaluation results |
|---|---|---|
| High-molecular compound | Polyvinylpyrrolidone | x |
| | Copolyvidone | x |
| | Methylcellulose | x |
| | Gum arabic | x |
| | Gelatin | o |
| | Hydroxypropyl methylcellulose | o |
| | Hydroxypropylcellulose | o |
| | Pullulan | o |
| | Agar | o |
| | PVA copolymer | o |
| | PVA | o |
| Plasticizer | Glycerol | x |
| | Triethyl citrate | x |
| | Propylene glycol | x |
| | Triacetin | x |
| | Polysorbate 80 | x |
| | Sorbitol | o |
| | Medium-chain triglyceride | o |
| | Sesame oil | o | o: not dissolved
x: dissolved

The results show that among the film-forming high-molecular compounds, the gelatin, hydroxypropyl methylcellulose, hydroxypropylcellulose, pullulan, agar, PVA copolymer, and PVA are insoluble in PEG; and among the plasticizers, the sorbitol, medium-chain triglyceride, and sesame oil were insoluble in PEG. Thus, these film-forming high-molecular compounds and plasticizers were evaluated as substances (candidates) usable as the raw-materials for the band seal.

Experimental Example 2

Selection of Raw Materials for the Band Seal (Part 2)

Based on the results of Experimental Example 1, the candidates as raw materials for the band seal (see Table 2) were tested to research substances soluble in an aqueous solution of a PVA copolymer (POVACOAT Type F, product of Daido Kasei Corp., viscosity: 5.5 mPa·s, as measured at 25° C. using a 5% aqueous solution of the copolymer), and an aqueous solution of PVA (JP-05, product of Japan Vam & Poval Co., Ltd., average degree of polymerization: 500).

More specifically, 0.5 g each of the film-forming high-molecular compounds and plasticizers were placed into separate test tubes. A 10 wt. % aqueous solution of the PVA copolymer or a 10 wt. % aqueous solution of the PVA was added to each test tube. After stirring with a mixer, the resulting mixtures were observed with the naked eye and evaluated for their solubility in the aqueous PVA copolymer solution and the aqueous PVA solution. If no solids or no liquid separation was observed with the naked eye, the mixture was evaluated as "dissolved". If some solids or liquid separation was observed, the mixture was evaluated as "not dissolved (insoluble)". The results are shown in Table 2.

TABLE 2

Test Results of Solubility in the Aqueous PVA Copolymer Solution and the Aqueous PVA Solution

| | | Evaluation result | |
|---|---|---|---|
| | Test substance | PVA copolymer | PVA |
| High-molecular compound | Gelatin | X | X |
| | Hydroxypropyl methylcellulose | X | X |
| | Hydroxypropylcellulose | X | X |
| | Pullulan | X | X |
| | Agar | X | X |
| | PVA copolymer | | ○ |
| | PVA | ○ | |
| Plasticizer | Sorbitol | ○ | ○ |
| | Medium-chain triglyceride | X | X |
| | Sesame oil | X | X |

○: not dissolved
X: dissolved

The results show that as raw materials for the band seal, the PVA copolymer and PVA can be used as film-forming high-molecular compounds, and sorbitol can be used as a plasticizer.

Experimental Example 3

Viscosity Appropriateness Test

Aqueous solutions of the PVA copolymer and PVA, which were evaluated as usable as raw materials for the band seal (film-forming, high-molecular compounds) in Experimental Example 2, were prepared and their appropriate viscosity as the band seal was determined according to the following method.

The PVA copolymers used were POVACOAT Type F (having a viscosity of 5.5 mPa·s as measured at 25° C. using a 5% aqueous solution of the copolymer), and POVACOAT Type R (having a viscosity of 20 mPa·s as measured at 25° C. using a 5% aqueous solution of the copolymer), both manufactured by Daido Kasei Corp. The PVA products used were JP-04 (having an average degree of polymerization of 400, partially saponified PVA: saponification degree 86 to 90 mol %); JP-05 (having an average degree of polymerization of 500, partially saponified PVA: saponification degree 87 to 89 mol %); JP-10 (having an average degree of polymerization of 1,000, partially saponified PVA: saponification degree 86 to 90 mol %); JP-15 (having an average degree of polymerization of 1,500, partially saponified PVA: saponification degree 86 to 90 mol %); JP-18 (having an average degree of polymerization of 1,800, partially saponified PVA: saponification degree 87 to 89 mol %); JP-20 (having an average degree of polymerization of 2,000, partially saponified PVA: saponification degree 87 to 89 mol %); and JP-33 (having an average degree of polymerization of 3,300, partially saponified PVA: saponification degree 86.5 to 89.5 mol %) all manufactured by Japan Vam & Poval Co., Ltd. The viscosity was measured with a B-type rotational viscometer (using a No. 2 rotor for a viscosity of less than 500 mPa·s, a No. 3 rotor for a viscosity of at least 500 mPa·s and less than 2,000 mPa·s, and a No. 4 rotor for a viscosity of 2,000 mPa·s or more) at 23° C. at 60 rpm for 1 minute.

More specifically, aqueous solutions of the PVA copolymers and PVA were prepared at concentrations as shown in Tables 3 to 11. The viscosity of the solutions was measured, and the solutions were also evaluated for viscosity appropriateness in terms of handling factors such as dripping, thread formation, and fluidity, when applied to hard capsules.

More specifically, if the solution was satisfactory in terms of dripping, thread formation, and fluidity, i.e., met all the requirements when applied to hard capsules, it was evaluated as "appropriate: O"; if the solution did not meet at least one of the above requirements, it was evaluated as "inappropriate: x".

Tables 3 to 11 show the results.

TABLE 3

Test Results of Viscosity Appropriateness of a PVA Copolymer (POVACOAT Type F)

| | Concentration (wt. %) | | | | |
|---|---|---|---|---|---|
| | 10 | 15 | 20 | 27 | 30 |
| Viscosity (mPa·s) | 20 | 120 | 470 | 4,800 | 11,000 |
| Viscosity appropriateness | x | ○ | ○ | ○ | x |

TABLE 4

Test Results of Viscosity Appropriateness of a PVA Copolymer (POVACOAT Type R)

| | Concentration (wt. %) | | | | |
|---|---|---|---|---|---|
| | 3 | 5 | 10 | 13 | 15 |
| Viscosity (mPa·s) | 70 | 130 | 850 | 4,200 | 8,000 |
| Viscosity appropriateness | x | ○ | ○ | ○ | x |

TABLE 5

Test Results of Viscosity Appropriateness of PVA (JP-04)

| | Concentration (wt. %) | | | | |
|---|---|---|---|---|---|
| | 10 | 15 | 25 | 31 | 33 |
| Viscosity (mPa·s) | 25 | 100 | 1,100 | 4,500 | 6,000 |
| Viscosity appropriateness | x | ○ | ○ | ○ | x |

TABLE 6

Test Results of Viscosity Appropriateness of PVA (JP-05)

| | Concentration (wt. %) | | | | |
|---|---|---|---|---|---|
| | 12 | 13 | 20 | 27 | 28 |
| Viscosity (mPa·s) | 80 | 130 | 900 | 4,800 | 6,900 |
| Viscosity appropriateness | x | ○ | ○ | ○ | x |

TABLE 7

Test Results of Viscosity Appropriateness of PVA (JP-10)

| | Concentration (wt. %) | | | | |
|---|---|---|---|---|---|
| | 8 | 10 | 15 | 20 | 22 |
| Viscosity (mPa·s) | 70 | 160 | 950 | 5,000 | 9,500 |
| Viscosity appropriateness | x | ○ | ○ | ○ | x |

TABLE 8

Test Results of Viscosity Appropriateness of PVA (JP-15)

| | Concentration (wt. %) | | | | |
|---|---|---|---|---|---|
| | 6 | 8 | 13 | 15 | 16 |
| Viscosity (mPa·s) | 60 | 200 | 1,700 | 3,900 | 5,200 |
| Viscosity appropriateness | x | ○ | ○ | ○ | x |

TABLE 9

Test Results of Viscosity Appropriateness of PVA (JP-18)

| | Concentration (wt. %) | | | | |
|---|---|---|---|---|---|
| | 6 | 7 | 10 | 13 | 14 |
| Viscosity (mPa·s) | 90 | 180 | 900 | 4,300 | 6,100 |
| Viscosity appropriateness | x | ○ | ○ | ○ | x |

TABLE 10

Test Results of Viscosity Appropriateness of PVA (JP-20)

| | Concentration (wt. %) | | | | |
|---|---|---|---|---|---|
| | 5 | 7 | 10 | 12 | 13 |
| Viscosity (mPa·s) | 70 | 220 | 1,500 | 4,000 | 6,500 |
| Viscosity appropriateness | x | ○ | ○ | ○ | x |

TABLE 11

Test Results of Viscosity Appropriateness of PVA (JP-33)

| | Concentration (wt. %) | | | | |
|---|---|---|---|---|---|
| | 3 | 4 | 7 | 9 | 10 |
| Viscosity (mPa·s) | 30 | 120 | 1,800 | 4,300 | 6,600 |
| Viscosity appropriateness | x | ○ | ○ | ○ | x |

The results show that all the aqueous solutions of the PVA copolymers and PVA with a viscosity of 100 to 5,000 mPa·s (23° C.) did not drip, and were easy to handle with excellent fluidity and no inconvenient thread formation. The above results confirmed that band seal liquids with an appropriate viscosity (100 to 5,000 mPa·s, 23° C.) and ease of handling when applied to hard capsules can be obtained by adjusting the concentration of the aqueous solutions of the PVA copolymers and PVAs.

Experimental Example 4

Various kinds of sealed filled hard capsules as described below were prepared (Examples 1 to 5), and the band seals applied thereto were evaluated for handling (dripping, thread formation, and fluidity), and band sealing properties.

(1) Preparation of Sealed Hard Capsule (1-1) Example 1

A solution of 25% of a PVA copolymer (POVACOAT Type F, product of Daido Kasei Corp.), 50.7% of water, and 24.3% of absolute ethanol (viscosity: 3,100 mPa·s as measured under the same conditions as in Experimental Example 3; the same applied hereinafter) was prepared and used as a band seal-preparation liquid. Using a fully automatic capsule-filling and sealing machine (product of Qualicaps Co., Ltd.), about 600 μL of a polyethylene glycol having an average molecular weight of 400 (PEG400) was filled in a Size No. 0 hard capsule comprising a PVA copolymer as a base material. The fitting portion of the body and cap of the hard capsule was sealed with the band seal-preparation liquid to produce a hard capsule filled with PEG.

The Size No. 0 hard capsule comprising a PVA copolymer as a base material was prepared according to the following method:

0.8 kg of a 10% aqueous potassium chloride solution, 8 kg of a 2% aqueous carrageenan solution, and 3.86 kg of purified water were added to 87.34 kg of a 22.9% aqueous solution of a PVA copolymer (POVACOAT Type L, product of Daido Kasei Corp., having a viscosity of 20 mPa·s as measured at 25° C. using a 5% aqueous solution thereof) heated to 60° C., and stirred. This solution was degassed while gently stirred for 24 hours. The thus obtained aqueous solution (capsule-preparation solution) was placed as an immersion fluid into a capsule manufacturing machine according to an immersion method. While the temperature of the immersion fluid was maintained at 50° C. to 55° C., the Size No. 0 hard capsule (cap and body) was prepared according to a usual method.

(1-2) Example 2

A solution (viscosity: 500 mPa·s) comprising 20% of a PVA copolymer (POVACOAT Type F, product of Daido Kasei Corp.), 2% of sorbitol, 50.7% of water, and 27.3% of absolute ethanol was prepared and used as a band seal-preparation liquid. Using a fully automatic capsule-filling and sealing machine (product of Qualicaps Co., Ltd.), about 600 μL of PEG400 was filled in a Size No. 0 hard capsule comprising a PVA copolymer as a base material. The fitting portion of the body and cap of the hard capsule was sealed with the band seal-preparation liquid to produce a hard capsule filled with PEG.

(1-3) Example 3

A solution (viscosity: 160 mPa·s) comprising 10% of a PVA copolymer (POVACOAT Type F, product of Daido Kasei Corp.), 10% of PVA (JP-05, product of Japan Vam & Poval Co., Ltd.), 2% of sorbitol, 50.7% of water, and 27.3% of absolute ethanol was prepared and used as a band seal-preparation liquid. Using a fully automatic capsule-filling and sealing machine (Qualicaps Co., Ltd.), about 600 μL of PEG400 was filled in a Size No. 0 hard capsule comprising a PVA copolymer as a base material. The fitting portion of the body and cap of the hard capsule was sealed with the band seal-preparation liquid to produce a hard capsule filled with PEG.

(1-4) Example 4

A solution (viscosity: 920 mPa·s) comprising 20% of PVA (JP-05, product of Japan Vam & Poval Co., Ltd.), 2% of sorbitol, 50.7% of water, and 27.3% of absolute ethanol was prepared and used as a band seal-preparation liquid. Using a fully automatic capsule-filling and sealing machine (Qualicaps Co., Ltd.), about 470 µL of PEG400 was filled in a Size No. 1 hard capsule comprising PVA as a base material. The fitting portion of the body and cap of the hard capsule was sealed with the band seal-preparation liquid to produce a hard capsule filled with PEG.

The Size No. 1 hard capsule comprising PVA as a base material was prepared according to the following method:

20 kg of PVA (average degree of polymerization: 1,000, saponification degree: 86-90 mol %, product of Wako Pure Chemical Industries, Ltd.) was added to 71.2 L of 40° C. purified water, and dispersed. The dispersion was heated to 82° C. to dissolve the PVA. This solution was cooled to 60° C. to prepare an aqueous PVA solution. 0.8 kg of a 10% aqueous potassium chloride solution and 8 kg of a 2% aqueous carrageenan solution were added to the aqueous PVA solution and stirred. This solution was degassed while gently stirred for 24 hours. The thus obtained aqueous capsule-preparation solution was placed as an immersion fluid into a capsule manufacturing machine according to an immersion method. While the temperature of the immersion fluid was maintained at 50° C. to 55° C., the Size No. 1 hard capsule (cap and body) was prepared according to a usual method.

(1-5) Example 5

A solution (viscosity: 500 mPa·s) comprising 20% of a PVA (JP-05, product of Japan Vam & Poval Co., Ltd.), 50.7% of water, and 29.3% of absolute ethanol was prepared and used as a band seal-preparation liquid. Using a fully automatic capsule-filling and sealing machine (product of Qualicaps Co., Ltd.), about 470 µL of PEG400 was filled in a Size No. 1 hard capsule comprising a PVA as a base material (see Example 4). The fitting portion of the body and cap of the hard capsule was sealed with the band seal-preparation liquid to produce a hard capsule filled with PEG.

(2) Evaluation of Handling and Band Sealing Properties (2-1) Evaluation of Handling (Dripping, Thread Formation, and Fluidity)

The viscosity of the band seal-preparation liquids used to prepare the sealed hard capsules of Example 1 to 5 was measured, and the liquids were also evaluated for dripping, thread formation, and fluidity. More specifically, if the liquid was satisfactory in terms of dripping, thread formation, and fluidity, i.e., met all the requirements when applied to hard capsules, the liquid was evaluated as "appropriate: O"; if the liquid did not meet at least one of the above requirements, it was evaluated as "inappropriate: x". Table 12 below shows the results. The results show that the band seal-preparation liquids did not form a thread, and when applied to the circumference of the fitting portion of the capsule, the band seal-preparation liquids did not drip, and an excellent band seal was easily formed.

(2-2) Evaluation of Band Sealing Properties

The sealed hard capsules prepared in Examples 1 to 5 were left at 23° C. at a relative humidity of 43% (RH43%) for one day, and then observed for changes in appearance, particularly the condition of the band seal formed on the circumference of the fitting portion. As a result, no content leakage from the sealed hard capsules prepared in Examples 1 to 5 was observed, and no appearance abnormalities were observed in the sealed portion (band seal portion).

The sealed hard capsules prepared in Example 1 to 5 were left on a white paper at 25° C. at a relative humidity of 40% for 12 hours, and content leakage (PEG400) from the band seal portion was then checked and evaluated according to the following method and criteria.

(a) After the sealed hard capsule was left for 12 hours, whether any adhesion of the content (PEG400) was observed on the area of the white paper in contact with the capsule.

(b) When the sealed hard capsule was rolled on the white paper after being left on the paper for 12 hours, whether any adhesion of the content (PEG400) was observed on the white paper.

If no adhesion of the content to the white copy paper, i.e., no content leakage was observed in (a) and (b), the liquid was evaluated as "having band sealing properties: O". If any content leakage was observed in (a) or (b), the solution was evaluated as "having no band sealing properties: x".

Table 12 below shows the results.

The results show that the contents did not leak from the sealed filled hard capsules (Examples 1 to 5) and that the band seals used have band sealing properties.

TABLE 12

| | (wt. %) | | | | |
| --- | --- | --- | --- | --- | --- |
| | Example 1 | Example 2 | Example 3 | Example 4 | Example 5 |
| PVA copolymer | 25.0 (100) ** | 20.0 (91) | 10.0 (45.5) | — (0) | — (0) |
| PVA | — (0) | — (0) | 10.0 (45.5) | 20.0 (91) | 20.0 (100) |
| Sorbitol | — (0) | 2.0 (9) | 2.0 (9) | 2.0 (9) | — (0) |
| Water | 50.7 | 50.7 | 50.7 | 50.7 | 50.7 |
| Absolute ethanol | 24.3 | 27.3 | 27.3 | 27.3 | 29.3 |
| Viscosity (mPa · s) * | 3,100 | 500 | 160 | 920 | 500 |
| Handling | o | o | o | o | o |
| Band sealing properties | o | o | o | o | o |

* Viscosity: measured with a B-type rotational viscometer (using a No. 2 rotor for a viscosity of less than 500 mPa · s, a No. 3 rotor for a viscosity of at least 500 mPa · s and less than 2,000 mPa · s, and a No. 4 rotor for a viscosity of 2,000 mPa · s or more) at 23° C. at 60 rpm for 1 minute.
** The numbers in parentheses in the table refer to the weight ratios of the PVA polymer, PVA, and sorbitol, based on the dry weight of the band seal as 100 wt. %.

Experimental Example 5

Using a PVA copolymer (POVACOAT Type F, product of Daido Kasei Corp.), PVA (JP-05, product of Japan Vam & Poval Co., Ltd.), and sorbitol as raw materials for the band seal, the band seal-preparation liquids of the formulations shown below in Table 13 (Formulation Examples 1 to 19) were prepared according to the methods of Examples 1 to 5. The numbers in parentheses in the table refer to the weight ratios of the PVA polymer, PVA, and sorbitol, based on the dry weight of the band seal as 100 wt. %. The viscosity of the band seal-preparation liquids was measured, and the liquids were also evaluated for handling, in terms of dripping, thread formation, and fluidity, when applied to hard capsules, according to the methods of Experimental Example 4.

Using a fully automatic capsule-filling and sealing machine (product of Qualicaps Co., Ltd.), about 470 μL of PEG400 was filled in a Size No. 1 hard capsule comprising a PVA as a base material (see Example 3). The fitting portion of the body and cap of the hard capsule was sealed with the band seal-preparation liquid to produce a hard capsule filled with PEG. The sealed hard capsule was observed with the naked eye to check the occurrence of content leakage and precipitation of sorbitol. After the sealed hard capsule was left on a white copy paper at 25° C. at a relative humidity of 40% for 12 hours in the same manner as in Example 4, the band sealing properties were evaluated in terms of whether content leakage occurred.

Table 13 also shows the results.

TABLE 13

|  | Formulation Example 1 | Formulation Example 2 | Formulation Example 3 | Formulation Example 4 | Formulation Example 5 | Formulation Example 6 |
|---|---|---|---|---|---|---|
| PVA copolymer | 25.0 (100) | 20 (91) | 10 (45.5) | — (0) | — (0) | 15 (80) |
| PVA | — (0) | — (0) | 10 (45.5) | 20 (91) | 20.0 (100) | — (0) |
| Sorbitol | — (0) | 2 (9) | 2 (9) | 2 (9) | — (0) | 3.75 (20) |
| Water | 50.7 | 50.7 | 50.7 | 50.7 | 50.7 | 50.7 |
| Absolute ethanol | 24.3 | 27.3 | 27.3 | 27.3 | 29.3 | 30.5 |
| Viscosity (mPa·s) | 3100 | 500 | 160 | 920 | 500 | 150 |
| Handling of the band seal-preparation liquid | ○ | ○ | ○ | ○ | ○ | ○ |
| Band sealing properties | ○ | ○ | ○ | ○ | ○ | ○ |
| Precipitation of sorbitol | Not occurred | Not occurred | Not occurred | Not occurred | Not occurred | Not occurred |

|  | Formulation Example 7 | Formulation Example 8 | Formulation Example 9 | Formulation Example 10 | Formulation Example 11 | Formulation Example 12 |
|---|---|---|---|---|---|---|
| PVA copolymer | 15.0 (70) | 15.0 (60) | 15.0 (50) | 15.0 (40) | 15.0 (30) | 10.0 (20) |
| PVA | — (0) | — (0) | — (0) | — (0) | — (0) | — (0) |
| Sorbitol | 6.4 (30) | 10.0 (40) | 15.0 (50) | 22.5 (60) | 35.0 (70) | 40.0 (80) |
| Water | 50.7 | 50.7 | 50.7 | 50.7 | 50.0 | 50.0 |
| Absolute ethanol | 27.9 | 24.3 | 19.3 | 11.8 | 0 | 0 |
| Viscosity (mPa·s) | 180 | 200 | 320 | 480 | 1600 | 220 |
| Handling of the band seal-preparation liquid | ○ | ○ | ○ | ○ | ○ | ○ |
| Band sealing properties | ○ | ○ | ○ | ○ | ○ | x |
| Precipitation of sorbitol | Not occurred | Occurred | Occurred | Occurred | Occurred | Not occurred |

|  | Formulation Example 13 | Formulation Example 14 | Formulation Example 15 | Formulation Example 16 | Formulation Example 17 | Formulation Example 18 | Formulation Example 19 |
|---|---|---|---|---|---|---|---|
| PVA copolymer | — (0) | — (0) | — (0) | — (0) | — (0) | — (0) | — (0) |
| PVA | 15.0 (80) | 15.0 (70) | 15.0 (60) | 15.0 (50) | 15.0 (40) | 15.0 (30) | 10.0 (20) |
| Sorbitol | 3.75 (20) | 6.4 (30) | 10.0 (40) | 15.0 (50) | 22.5 (60) | 35.0 (70) | 40.0 (80) |
| Water | 50.7 | 50.7 | 50.7 | 50.7 | 50.7 | 50.0 | 50.0 |
| Absolute ethanol | 30.5 | 27.9 | 24.3 | 19.3 | 11.8 | 0 | 0 |
| Viscosity (mPa·s) | 180 | 250 | 300 | 600 | 800 | 2000 | 350 |
| Handling of the band seal-preparation liquid | ○ | ○ | ○ | ○ | ○ | ○ | ○ |
| Band sealing properties | ○ | ○ | ○ | ○ | ○ | ○ | x |
| Precipitation of sorbitol | Not occurred | Not occurred | Occurred | Occurred | Occurred | Occurred | Occurred |

The above results show that the PVA and PVA copolymers are suitable for use as raw materials for the band seal, and can be used singly or in combination; and even when the starting composition comprises sorbitol in a proportion of 70% or less, the composition can be suitably used as the raw material for the band seal. From the viewpoint of band sealing properties, the proportion of sorbitol may be any amount that is not more than 70%. From the viewpoint of the precipitation of sorbitol, the proportion is preferably less than 40%, more preferably not more than 35%, and even more preferably not more than 30%.

EFFECT OF THE INVENTION

The use of the band seal of the invention can prevent content leakage through the gap between the body and cap of a hard capsule filled with PEG, particularly a composition comprising a low-molecular-weight PEG having an average molecular weight of 200 to 600, and also protect the contents from deterioration caused by contact with air and water that enter through the gap.

According to the filled hard capsule of the invention, the cap-to-body fitting portion of the capsule is sealed with the band seal. Therefore, even when the hard capsule is filled with PEG, particularly a composition comprising a low-molecular-weight PEG with an average molecular weight of 200 to 600, the contents of the capsule do not leak through the gap between the body and the cap, and deterioration of the contents caused by contact with air and water that enter through the gap can also be prevented. Thus, the hard capsule is useful as a capsule to contain a drug, quasi drug, cosmetic, or food composition comprising PEG, particularly a low-molecular-weight PEG having an average molecular weight of 200 to 600, as an excipient.

The invention claimed is:

1. A filled hard capsule comprising a film, a filling material and a band seal,
    wherein the film comprises a polyvinyl alcohol, a polyvinyl alcohol copolymer or a mixture thereof;
    wherein the filling material comprises a polyethylene glycol or a composition comprising a polyethylene glycol;
    wherein the band seal comprises a polyvinyl alcohol, a polyvinyl alcohol copolymer, or a mixture thereof, and optionally sorbitol; and
    wherein each polyvinyl alcohol and each polyvinyl alcohol copolymer is composed of a partially saponified polyvinyl alcohol with a saponification degree of 78 to 90 mol %;
    with the proviso that the band seal does not comprise polyvinylpyrrolidone or a copolymer of N-vinylpyrrolidone, and
    with the proviso that the band seal does not comprise polyvinyl alcohol with a gelling agent.

2. The filled hard capsule according to claim 1, wherein the polyethylene glycol is a low-molecular-weight polyethylene glycol having an average molecular weight of 200 to 600.

3. The filled hard capsule according to claim 1, wherein the film further comprises a gelling agent, or a gelling agent and a gelling aid.

4. A process for preparing the filled hard capsule of claim 1, the process comprising:
    inserting the filling material comprising polyethylene glycol or a composition comprising a polyethylene glycol into a hard capsule, wherein the hard capsule is formed of the film comprising a polyvinyl alcohol, a polyvinyl alcohol copolymer or a mixture thereof,
    fitting a cap onto a body of the capsule,
    applying a band seal-preparation liquid comprising a polyvinyl alcohol, a polyvinyl alcohol copolymer, or a mixture thereof, and optionally sorbitol,
    wherein each polyvinyl alcohol and each polyvinyl alcohol copolymer is composed of a partially saponified polyvinyl alcohol with a saponification degree of 78 to 90 mol %;
    with the proviso that the band seal does not comprise polyvinylpyrrolidone or a copolymer of N-vinylpyrrolidone, and
    with the proviso that the band seal does not comprise polyvinyl alcohol with a gelling agent,
    and drying to seal the capsule.

5. The process according to claim 4, wherein the polyethylene glycol is a low-molecular-weight polyethylene glycol having an average molecular weight of 200 to 600.

6. The process according to claim 4, wherein the film further comprises a gelling agent, or a gelling agent and a gelling aid.

7. The filled hard capsule according to claim 1, wherein the band seal comprises a polyvinyl alcohol, a polyvinyl alcohol copolymer and sorbitol; and wherein the polyvinyl alcohol and polyvinyl alcohol copolymer are composed of a partially saponified polyvinyl alcohol with a saponification degree of 78-90 mol %.

8. The process for preparing a filled hard capsule according to claim 4, wherein the band seal-preparation liquid is an aqueous solution comprising a polyvinyl alcohol, a polyvinyl alcohol copolymer, and sorbitol, and wherein the polyvinyl alcohol and polyvinyl alcohol copolymer are composed of a partially saponified polyvinyl alcohol with a saponification degree of 78-90 mol %.

9. The process for preparing a filled hard capsule according to claim 4, wherein the band seal-preparation liquid has a viscosity of 100 to 5,000 mPa·s, as measured with a B-type rotational viscometer (using a No. 2 rotor for a viscosity of less than 500 mPa·s, a No. 3 rotor for a viscosity of at least 500 mPa·s and less than 2,000 mPa·s, and a No. 4 rotor for a viscosity of 2000 mPa·s or more) at 23° C. at 60 rpm for 1 minute.

10. The process for preparing a filled hard capsule according to claim 4, wherein the hard capsule has a body adapted to receive a cap.

11. The filled hard capsule according to claim 1, wherein each polyvinyl alcohol and each polyvinyl alcohol copolymer is composed of a partially saponified polyvinyl alcohol with a saponification degree of 87 to 90 mol %.

12. The process for preparing a filled hard capsule according to claim 4, wherein each polyvinyl alcohol and each polyvinyl alcohol copolymer is composed of a partially saponified polyvinyl alcohol with a saponification degree of 87 to 90 mol %.

13. The filled hard capsule according to claim 1, wherein the band seal consists of a polyvinyl alcohol copolymer composed of a partially saponified polyvinyl alcohol with a saponification degree of 78-90 mol %.

14. The filled hard capsule according to claim 1, wherein the band seal comprises a mixture of polyvinyl alcohol and polyvinyl alcohol copolymer; and wherein the polyvinyl alcohol and polyvinyl alcohol copolymer are composed of a partially saponified polyvinyl alcohol with a saponification degree of 78-90 mol %.

* * * * *